(12) United States Patent
Hooven (10) Patent No.: US 6,896,673 B2
(45) Date of Patent: May 24, 2005

(54) METHOD FOR TRANSMURAL ABLATION (75) Inventor: Michael D. Hooven, Cincinnati, OH (US)

(73) Assignee: AtriCure, Inc., West Chester, OH (US)

( * ) Notice: Subject to any disclaimer, the term of this patent is extended or adjusted under 35 U.S.C. 154(b) by 0 days.

(21) Appl. No.: 10/327,831

(22) Filed: Dec. 23, 2002

(65) Prior Publication Data

US 2003/0093068 A1 May 15, 2003

Related U.S. Application Data (63) Continuation of application No. 09/747,609, filed on Dec. 22, 2000, now Pat. No. 6,546,935.
(60) Provisional application No. 60/200,072, filed on Apr. 27, 2000.

(51) Int. Cl.⁷ .............................................. A61B 18/18
(52) U.S. Cl. .............................. 606/32; 606/41; 606/49; 606/51; 606/52
(58) Field of Search ............................ 606/32, 34, 35, 606/39–42, 46–52; 607/96, 98, 99, 100, 101–113, 115, 116, 114; 128/898

(56) References Cited

U.S. PATENT DOCUMENTS

| | | |
|---|---|---|
| 1,127,948 A | 2/1915 | Wappler |
| 2,004,559 A | 6/1935 | Wappler et al. |
| 3,470,875 A | 10/1969 | Johnson et al. |
| 3,630,207 A | 12/1971 | Kahn et al. ................. 128/350 |
| 3,901,242 A | 8/1975 | Storz ......................... 128/303 |
| 4,043,342 A | 8/1977 | Morrison, Jr. .............. 128/303 |
| 4,312,337 A | 1/1982 | Donohue et al. |
| 4,353,371 A | 10/1982 | Cosman ..................... 128/303 |
| 4,492,231 A | 1/1985 | Auth .......................... 128/303 |
| 4,590,934 A | 5/1986 | Malis et al. ................ 128/303 |
| 4,706,667 A | 11/1987 | Roos .......................... 128/303 |
| 4,732,149 A | 3/1988 | Sutter ......................... 128/303 |
| 4,802,475 A | 2/1989 | Weshahy ..................... 128/303 |
| 4,940,064 A | 7/1990 | Desai ......................... 128/784 |
| 5,009,661 A | 4/1991 | Michelson |
| 5,013,312 A | 5/1991 | Parins et al. ................. 606/37 |
| 5,033,477 A | 7/1991 | Chin et al. |

(Continued)

FOREIGN PATENT DOCUMENTS

| | | |
|---|---|---|
| DE | 43 13 903 C1 | 9/1994 |
| EP | 0 450 608 A1 | 10/1991 |
| EP | 0 765 639 | 4/1997 |

(Continued)

OTHER PUBLICATIONS

English abstract re Japanese Patent Application No. JP 1996000275351, published Apr. 28, 1997.

Yoshio Kosakai, M.D., et al., "Cox Maze Procedure for Chronic Atrial Fibrillation Associated with Mitral Valve Disease," The Journal of Thoracic and Cardiovascular Surgery, 1994; vol. 108, No. 6, pp. 1049–1055.

Ki–Bong Kim, M.D., et al., Abstract "The Cox–Maze III Procedure for Atrial Fibrillation Associated with Rheumatic Mitral Valve Disease," The Annals of Thoracic Surgery, 2000; pp. 1–5.

(Continued)

Primary Examiner—Rosiland Rollins
(74) Attorney, Agent, or Firm—Cook, Alex, McFarron, Manzo, Cummings & Mehler, Ltd.

(57) ABSTRACT

A method for transmural ablation using an instrument containing two electrodes or cryogenic probes. A clamping force is exerted on the two electrodes or probes such that the tissue of the hollow organ is clamped therebetween. Bipolar RF energy is then applied between the two electrodes, or the probes are cryogenically cooled, thus ablating the tissue therebetween. A monitoring device measures a suitable parameter, such as impedance or temperature, and indicates when the tissue between the electrodes has been fully ablated.

21 Claims, 7 Drawing Sheets

U.S. PATENT DOCUMENTS

| | | |
|---|---|---|
| 5,044,947 A | 9/1991 | Sachdeva et al. |
| 5,071,428 A | 12/1991 | Chin et al. |
| 5,083,565 A | 1/1992 | Parins ........................ 128/642 |
| 5,085,657 A | 2/1992 | Ben-Simhon ................ 606/42 |
| 5,087,243 A | 2/1992 | Avitall ........................ 604/20 |
| 5,116,332 A | 5/1992 | Lottick ........................ 606/42 |
| 5,125,928 A | 6/1992 | Parins et al. |
| 5,147,355 A | 9/1992 | Friedman .................... 606/23 |
| 5,190,541 A | 3/1993 | Abele et al. ................. 606/46 |
| 5,207,691 A | 5/1993 | Nardella .................... 606/142 |
| 5,217,460 A | 6/1993 | Knopfler ...................... 606/52 |
| 5,231,995 A | 8/1993 | Desai ......................... 128/784 |
| 5,242,441 A | 9/1993 | Avitall ........................ 606/41 |
| 5,242,458 A | 9/1993 | Bendel et al. |
| 5,250,047 A | 10/1993 | Rydell ........................ 606/48 |
| 5,250,075 A | 10/1993 | Badie .......................... 606/207 |
| 5,254,130 A | 10/1993 | Poncet et al. |
| 5,263,493 A | 11/1993 | Avitall ........................ 607/122 |
| 5,269,326 A | 12/1993 | Verrier ....................... 128/642 |
| 5,269,780 A | 12/1993 | Roos ............................ 606/42 |
| 5,281,215 A | 1/1994 | Milder ........................ 606/20 |
| 5,281,216 A | 1/1994 | Klicek ........................ 606/42 |
| 5,293,869 A | 3/1994 | Edwards et al. ........... 128/642 |
| 5,306,234 A | 4/1994 | Johnson |
| 5,318,589 A | 6/1994 | Lichtman ................... 606/205 |
| 5,323,781 A | 6/1994 | Ideker et al. |
| 5,327,905 A | 7/1994 | Avitall ........................ 128/772 |
| 5,354,297 A | 10/1994 | Avitall ........................ 606/45 |
| 5,357,956 A | 10/1994 | Nardella .................... 128/642 |
| 5,397,339 A | 3/1995 | Desai ......................... 607/116 |
| 5,403,312 A | 4/1995 | Yates et al. .................. 606/50 |
| 5,423,807 A | 6/1995 | Milder ........................ 606/20 |
| 5,429,131 A | 7/1995 | Scheinman et al. ........ 128/642 |
| 5,429,636 A | 7/1995 | Shikhman et al. .......... 606/41 |
| 5,438,302 A | 8/1995 | Goble ........................ 331/167 |
| 5,441,483 A | 8/1995 | Avitall ........................ 604/95 |
| 5,443,463 A | 8/1995 | Stern et al. .................. 606/51 |
| 5,445,638 A | 8/1995 | Rydell et al. ................ 606/51 |
| 5,449,355 A | 9/1995 | Rhum et al. ................. 606/41 |
| 5,451,223 A | 9/1995 | Ben-Simhon ................ 606/42 |
| 5,452,733 A | 9/1995 | Sterman et al. |
| 5,454,370 A | 10/1995 | Avitall ........................ 128/642 |
| 5,465,716 A | 11/1995 | Avitall ........................ 128/642 |
| 5,472,441 A | 12/1995 | Edwards et al. ............ 606/41 |
| 5,478,309 A | 12/1995 | Sweezer et al. .............. 604/4 |
| 5,480,409 A | 1/1996 | Riza .......................... 606/205 |
| 5,487,385 A | 1/1996 | Avitall ........................ 128/642 |
| 5,496,312 A | 3/1996 | Klicek ........................ 606/34 |
| 5,500,011 A | 3/1996 | Desai ......................... 607/116 |
| 5,500,012 A | 3/1996 | Brucker et al. |
| 5,531,744 A | 7/1996 | Nardella et al. ............ 606/48 |
| 5,536,267 A | 7/1996 | Edwards et al. ............ 606/41 |
| 5,549,636 A | 8/1996 | Li |
| 5,555,883 A | 9/1996 | Avitall ........................ 128/642 |
| 5,562,699 A | 10/1996 | Heimberger et al. |
| 5,562,700 A | 10/1996 | Huitema et al. |
| 5,562,721 A | 10/1996 | Marchlinski et al. ........ 607/99 |
| 5,564,440 A | 10/1996 | Swartz et al. ............... 128/898 |
| 5,571,215 A | 11/1996 | Sterman et al. |
| 5,575,766 A | 11/1996 | Swartz et al. |
| 5,575,805 A | 11/1996 | Li |
| 5,582,609 A | 12/1996 | Swanson et al. ............. 606/39 |
| 5,587,723 A | 12/1996 | Otake et al. ................. 345/118 |
| 5,595,183 A | 1/1997 | Swanson et al. ............ 128/898 |
| 5,599,350 A | 2/1997 | Schulze et al. .............. 606/51 |
| 5,611,813 A | 3/1997 | Lichtman ................... 606/205 |
| 5,620,459 A | 4/1997 | Lichtman ................... 606/205 |
| 5,642,736 A | 7/1997 | Avitall ........................ 128/772 |
| 5,655,219 A | 8/1997 | Jusa et al. ................... 370/338 |
| 5,672,174 A | 9/1997 | Gough et al. ................ 606/41 |
| 5,674,220 A | 10/1997 | Fox et al. .................... 606/51 |
| 5,680,860 A | 10/1997 | Imran |
| 5,683,384 A | 11/1997 | Gough et al. ................ 606/41 |
| 5,687,737 A | 11/1997 | Branham et al. ........... 128/710 |
| 5,688,270 A | 11/1997 | Yates et al. .................. 606/51 |
| 5,690,611 A | 11/1997 | Swartz et al. ................ 604/53 |
| 5,693,051 A | 12/1997 | Schulze et al. .............. 606/51 |
| 5,697,925 A | 12/1997 | Taylor ........................ 606/34 |
| 5,697,928 A | 12/1997 | Walcott et al. ............... 606/41 |
| 5,702,359 A | 12/1997 | Hofmann et al. ............ 604/20 |
| 5,702,390 A | 12/1997 | Austin et al. ................ 606/48 |
| 5,702,438 A | 12/1997 | Avitall ........................ 607/122 |
| 5,709,680 A | 1/1998 | Yates et al. .................. 606/50 |
| 5,718,703 A | 2/1998 | Chin .......................... 606/49 |
| 5,722,403 A | 3/1998 | McGee et al. ............. 128/642 |
| 5,725,512 A | 3/1998 | Swartz et al. ............... 604/280 |
| 5,728,143 A | 3/1998 | Gough et al. ............... 607/101 |
| 5,730,127 A | 3/1998 | Avitall ........................ 128/642 |
| 5,730,704 A | 3/1998 | Avitall ........................ 600/374 |
| 5,733,280 A | 3/1998 | Avitall ........................ 606/23 |
| 5,735,847 A | 4/1998 | Gough et al. ................ 606/45 |
| 5,735,849 A | 4/1998 | Baden et al. ................ 606/51 |
| 5,740,808 A | 4/1998 | Panescu et al. ............ 128/662 |
| 5,755,664 A | 5/1998 | Rubenstein ................ 600/377 |
| 5,755,717 A | 5/1998 | Yates et al. .................. 606/51 |
| 5,759,158 A | 6/1998 | Swanson ..................... 600/508 |
| 5,776,130 A | 7/1998 | Buysse et al. |
| 5,782,827 A | 7/1998 | Gough et al. ................ 606/41 |
| 5,782,828 A | 7/1998 | Chen et al. .................. 606/42 |
| 5,785,706 A | 7/1998 | Bednarek .................... 606/41 |
| H1745 H | 8/1998 | Paraschac ................... 606/51 |
| 5,797,906 A | 8/1998 | Rhum et al. ................. 606/48 |
| 5,797,960 A | 8/1998 | Stevens et al. ............. 606/213 |
| 5,800,484 A | 9/1998 | Gough et al. ............... 607/104 |
| 5,807,393 A | 9/1998 | Williamson, IV et al. ..... 606/32 |
| 5,807,395 A | 9/1998 | Mulier et al. ................ 606/41 |
| 5,810,804 A | 9/1998 | Gough et al. ................ 606/41 |
| 5,810,805 A | 9/1998 | Sutcu et al. .................. 606/45 |
| 5,810,811 A | 9/1998 | Yates et al. .................. 606/50 |
| 5,814,028 A | 9/1998 | Swartz et al. |
| 5,817,091 A | 10/1998 | Nardella et al. ............. 606/38 |
| 5,823,955 A | 10/1998 | Kuck et al. ................. 600/374 |
| 5,823,956 A | 10/1998 | Roth et al. .................. 600/374 |
| 5,829,447 A | 11/1998 | Stevens et al. ............. 128/898 |
| 5,833,690 A | 11/1998 | Yates et al. .................. 606/52 |
| 5,833,703 A | 11/1998 | Manushakian .............. 606/174 |
| 5,842,984 A | 12/1998 | Avitall ........................ 600/374 |
| 5,843,075 A | 12/1998 | Taylor ........................ 606/34 |
| 5,843,122 A | 12/1998 | Riza .......................... 606/207 |
| 5,846,238 A | 12/1998 | Jackson et al. .............. 606/41 |
| 5,849,011 A | 12/1998 | Jones et al. .................. 606/47 |
| 5,849,020 A | 12/1998 | Long et al. ................. 606/167 |
| 5,853,411 A | 12/1998 | Whayne et al. .............. 606/41 |
| 5,855,590 A | 1/1999 | Malecki et al. |
| 5,855,614 A | 1/1999 | Stevens et al. .............. 623/11 |
| 5,860,975 A | 1/1999 | Goble et al. ................. 606/45 |
| 5,863,290 A | 1/1999 | Gough et al. ................ 606/41 |
| 5,863,291 A | 1/1999 | Schaer ........................ 606/41 |
| 5,868,737 A | 2/1999 | Taylor et al. ................. 606/34 |
| 5,871,483 A | 2/1999 | Jackson et al. .............. 606/41 |
| 5,873,896 A | 2/1999 | Ideker ........................ 607/14 |
| 5,876,398 A | 3/1999 | Mulier et al. |
| 5,876,400 A | 3/1999 | Songer ........................ 606/45 |
| 5,876,401 A | 3/1999 | Schulze et al. .............. 606/51 |
| 5,891,135 A | 4/1999 | Jackson et al. .............. 606/41 |
| 5,891,136 A | 4/1999 | McGee et al. ............... 606/41 |
| 5,891,138 A | 4/1999 | Tu et al. |
| 5,893,863 A | 4/1999 | Yoon .......................... 606/170 |
| 5,897,554 A | 4/1999 | Chia et al. |
| 5,899,898 A | 5/1999 | Arless et al. ................. 606/22 |
| 5,899,899 A | 5/1999 | Arless et al. ................. 606/22 |

| | | | |
|---|---|---|---|
| 5,902,289 A | 5/1999 | Swartz et al. ............... 604/281 |
| 5,910,129 A | 6/1999 | Koblish et al. ............... 604/95 |
| 5,913,855 A | 6/1999 | Gough et al. ................ 606/41 |
| 5,921,924 A | 7/1999 | Avitall ........................ 600/374 |
| 5,924,424 A | 7/1999 | Stevens et al. ............. 128/898 |
| 5,925,038 A | 7/1999 | Panescu et al. ............. 606/41 |
| 5,925,042 A | 7/1999 | Gough et al. ................ 606/41 |
| 5,928,229 A | 7/1999 | Gough et al. ................ 606/41 |
| 5,931,836 A | 8/1999 | Hatta et al. .................. 606/38 |
| 5,935,126 A | 8/1999 | Riza ........................... 606/51 |
| 5,938,660 A | 8/1999 | Swartz et al. ................ 606/45 |
| 5,941,251 A | 8/1999 | Panescu et al. ............. 128/899 |
| 5,941,845 A | 8/1999 | Tu et al. ....................... 604/53 |
| 5,944,718 A | 8/1999 | Austin et al. ................ 606/48 |
| 5,947,938 A | 9/1999 | Swartz et al. ............... 604/280 |
| 5,951,547 A | 9/1999 | Gough et al. ................ 606/41 |
| 5,951,552 A | 9/1999 | Long et al. .................. 606/46 |
| 5,954,665 A | 9/1999 | Ben-Haim .................. 600/515 |
| 5,961,514 A | 10/1999 | Long et al. .................. 606/41 |
| 5,967,976 A | 10/1999 | Larsen ........................ 600/374 |
| 5,971,983 A | 10/1999 | Lesh ........................... 606/41 |
| 5,972,026 A | 10/1999 | Laufer et al. ................ 607/96 |
| 5,980,516 A | 11/1999 | Mulier et al. ................ 606/41 |
| 5,980,517 A | 11/1999 | Gough ........................ 606/41 |
| 5,984,281 A | 11/1999 | Hacker et al. ............... 261/71 |
| 5,997,533 A | 12/1999 | Kuhns ........................ 606/41 |
| 6,010,516 A | 1/2000 | Hulka ......................... 606/148 |
| 6,010,531 A | 1/2000 | Donlon et al. ................ 623/2 |
| 6,012,457 A | 1/2000 | Lesh ........................... 128/898 |
| 6,013,074 A | 1/2000 | Taylor ........................ 606/34 |
| 6,016,809 A | 1/2000 | Mulier et al. ............... 128/898 |
| 6,017,358 A | 1/2000 | Yoon et al. .................. 606/205 |
| 6,023,638 A | 2/2000 | Swanson ..................... 600/510 |
| 6,024,740 A | 2/2000 | Lesh et al. ................... 606/34 |
| 6,024,741 A | 2/2000 | Williamson, IV et al. .... 606/40 |
| 6,030,403 A | 2/2000 | Long et al. .................. 606/185 |
| 6,033,402 A | 3/2000 | Tu et al. |
| 6,036,670 A | 3/2000 | Wijeratne et al. ............ 604/96 |
| 6,039,731 A | 3/2000 | Taylor et al. ................ 606/34 |
| 6,039,733 A | 3/2000 | Buyssee et al. .............. 606/40 |
| 6,039,748 A | 3/2000 | Savage et al. ............... 606/180 |
| 6,047,218 A | 4/2000 | Whayne et al. .............. 607/122 |
| 6,048,329 A | 4/2000 | Thompson et al. ........... 604/95 |
| 6,050,996 A | 4/2000 | Schmaltz et al. |
| 6,064,902 A | 5/2000 | Haissaguerre et al. |
| 6,068,653 A | 5/2000 | LaFontaine |
| 6,071,281 A | 6/2000 | Burnside et al. |
| 6,083,150 A | 7/2000 | Aznoian et al. |
| 6,083,222 A | 7/2000 | Klein et al. |
| 6,096,037 A | 8/2000 | Mulier et al. |
| 6,110,098 A | 8/2000 | Renirie et al. ............... 600/16 |
| 6,113,595 A | 9/2000 | Muntermann |
| 6,113,598 A | 9/2000 | Baker |
| 6,117,101 A | 9/2000 | Diederich et al. |
| 6,123,703 A | 9/2000 | Tu et al. |
| 6,126,658 A | 10/2000 | Baker |
| 6,142,994 A | 11/2000 | Swanson et al. |
| 6,156,033 A | 12/2000 | Tu et al. |
| 6,161,543 A | 12/2000 | Cox et al. |
| 6,162,220 A | 12/2000 | Nezhat |
| 6,193,713 B1 | 2/2001 | Geistert et al. |
| 6,237,605 B1 | 5/2001 | Vaska et al. |
| 6,264,087 B1 | 7/2001 | Whitman |
| 6,267,761 B1 | 7/2001 | Ryan |
| 6,273,887 B1 | 8/2001 | Yamauchi et al. |
| 6,277,117 B1 | 8/2001 | Tetzlaff et al. |
| 6,292,678 B1 | 9/2001 | Hall et al. |
| 6,296,640 B1 | 10/2001 | Wampler et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,332,089 B1 | 12/2001 | Acker et al. |
| 6,334,860 B1 | 1/2002 | Dorn |
| 6,356,790 B1 | 3/2002 | Maguire et al. |
| 6,358,249 B1 | 3/2002 | Chen et al. |
| 6,391,024 B1 | 5/2002 | Sun et al. |
| 6,443,970 B1 | 9/2002 | Schulze et al. |
| 6,447,507 B1 | 9/2002 | Bednarek et al. |
| 6,464,700 B1 | 10/2002 | Koblish et al. |
| 6,474,340 B1 | 11/2002 | Vaska et al. |
| 6,488,678 B2 | 12/2002 | Sherman |
| 6,488,680 B1 | 12/2002 | Francischelli et al. |
| 6,506,189 B1 | 1/2003 | Rittman, III et al. |
| 6,517,536 B2 | 2/2003 | Hooven |
| 6,540,740 B2 | 4/2003 | Lehmann et al. |
| 6,546,935 B2 | 4/2003 | Hooven |
| 6,575,969 B1 | 6/2003 | Rittman, III et al. |
| 6,610,055 B1 | 8/2003 | Swanson et al. |
| 6,632,222 B1 | 10/2003 | Edwards et al. |
| 6,679,882 B1 | 1/2004 | Kornerup |
| 6,692,491 B1 * | 2/2004 | Phan ........................... 606/51 |
| 2001/0031961 A1 | 10/2001 | Hooven |
| 2001/0039419 A1 | 11/2001 | Francischelli et al. |
| 2002/0002329 A1 | 1/2002 | Avitall |
| 2002/0019629 A1 | 2/2002 | Dietz et al. |
| 2002/0032440 A1 | 3/2002 | Hooven |
| 2002/0052602 A1 | 5/2002 | Wang et al. |
| 2002/0082595 A1 | 6/2002 | Langberg et al. |
| 2002/0091382 A1 | 7/2002 | Hooven |
| 2002/0091383 A1 | 7/2002 | Hooven |
| 2002/0091384 A1 | 7/2002 | Hooven |
| 2002/0099364 A1 | 7/2002 | Lalonde |
| 2002/0103484 A1 | 8/2002 | Hooven |
| 2002/0107513 A1 | 8/2002 | Hooven |
| 2002/0107514 A1 | 8/2002 | Hooven |
| 2002/0115990 A1 | 8/2002 | Acker |
| 2002/0115993 A1 | 8/2002 | Hooven |
| 2002/0120263 A1 | 8/2002 | Brown et al. |
| 2002/0120316 A1 | 8/2002 | Hooven |
| 2002/0128643 A1 | 9/2002 | Simpson et al. |
| 2002/0183738 A1 | 12/2002 | Chee et al. |
| 2003/0004507 A1 | 1/2003 | Francischelli et al. |
| 2003/0009094 A1 | 1/2003 | Segner et al. |
| 2003/0018329 A1 | 1/2003 | Hooven |
| 2003/0028187 A1 | 2/2003 | Vaska et al. |
| 2003/0032952 A1 | 2/2003 | Hooven |
| 2003/0045871 A1 | 3/2003 | Jain et al. |
| 2003/0050557 A1 | 3/2003 | Susil et al. |
| 2003/0060822 A1 | 3/2003 | Schaer et al. |
| 2003/0069572 A1 | 4/2003 | Wellman et al. |
| 2003/0069577 A1 | 4/2003 | Vaska et al. |
| 2003/0073991 A1 | 4/2003 | Francischelli et al. |
| 2003/0078570 A1 | 4/2003 | Heiner et al. |
| 2003/0078574 A1 | 4/2003 | Hall et al. |
| 2003/0093104 A1 | 5/2003 | Bonner et al. |
| 2003/0097124 A1 | 5/2003 | Lehmann et al. |
| 2003/0100895 A1 | 5/2003 | Simpson et al. |
| 2003/0114844 A1 | 6/2003 | Ormsby et al. |
| 2003/0120268 A1 | 6/2003 | Bertolero et al. |
| 2003/0125726 A1 | 7/2003 | Maguire et al. |
| 2003/0125729 A1 | 7/2003 | Hooven |
| 2003/0125730 A1 | 7/2003 | Berube et al. |
| 2003/0130598 A1 | 7/2003 | Manning et al. |
| 2003/0135207 A1 | 7/2003 | Langberg et al. |
| 2003/0144657 A1 | 7/2003 | Bowe et al. |
| 2003/0158548 A1 | 8/2003 | Phan et al. |
| 2003/0171745 A1 | 9/2003 | Francischelli et al. |
| 2003/0178032 A1 | 9/2003 | Ingle et al. |

FOREIGN PATENT DOCUMENTS

| | | |
|---|---|---|
| WO | WO 92/05828 A1 | 4/1992 |
| WO | WO 93/25267 A1 | 12/1993 |

| WO | WO 97/10764 A1 | 3/1997 |
| --- | --- | --- |
| WO | WO 97/32525 | 9/1997 |
| WO | WO 98/17187 | 4/1998 |
| WO | WO 98/53750 | 12/1998 |
| WO | WO 99/02096 | 1/1999 |
| WO | WO 99/04696 | 2/1999 |
| WO | WO 99/12487 | 3/1999 |
| WO | WO 99/44519 | 9/1999 |
| WO | WO 99/56486 | 11/1999 |
| WO | WO 99/56644 | 11/1999 |
| WO | WO 99/56648 | 11/1999 |
| WO | WO 99/59486 | 11/1999 |
| WO | WO 00/21449 | 4/2000 |
| WO | WO 00/27310 A3 | 5/2000 |
| WO | WO 00/27310 A2 | 5/2000 |
| WO | WO 00/27311 | 5/2000 |
| WO | WO 00/27312 | 5/2000 |
| WO | WO 00/27313 | 5/2000 |
| WO | WO 00/42931 | 7/2000 |
| WO | WO 00/42932 | 7/2000 |
| WO | WO 00/42933 | 7/2000 |
| WO | WO 00/42934 | 7/2000 |
| WO | WO 01/82812 A1 | 11/2001 |
| WO | WO 01/82813 A3 | 11/2001 |
| WO | WO 01/82813 A2 | 11/2001 |
| WO | WO 02/087454 A1 | 11/2002 |

OTHER PUBLICATIONS

Hiroshi Nakagawa, et al., Abstract, "Creation of Long Linear Transmural Radiofrequencey Lesions in Atrium Using a Novel Spiral Ribbon—Saline Irrigated Electrode Catheter," Journal of American College of Cardiology, Feb., 1996.

Taijiro Sueda, et al., "Efficacy of a Simple Left Atrial Procudure for Chronic Atrial Procedure for Chronic Atrial Fibrillation in Mitral Valve Operations," The Annals of Thoracic Surgery, 1997, vol. 63, pp. 1070–1073.

Re: Dr. Adam E. Saltman, New Program in Surgical Electrophysiology Established, Interet Website of Departmental News, Dept. of Surgery, University Hospital & Medical Center, Stony Brook State University of New York (www.informatics.synysb.edu/surgery/electro–news.html); 2000, pp. 1–2.

Mien–Cheng Chen, M.D., et al., "Radiofrequency and Cryoablation of Atrial Fibrillation in Patients Undergoing Valvular Operations," Anals of Thoracic Surgery, 1998:65:1666–1672.

Arif Elvan, M.D., et al., Abstract, "Radiofrequency Catheter Ablation of the Atria Reduces Inducibility and Duration of Atrial Fibrillation in Dogs," CIRCULATION, 1995:91:2235–2244.

Warren M. Jackman, M.D., et al.., "Radiofrequency Current Directed Across the Mitral Anulus With a Bipolar Epicardial–Endocardial Catheter Electrode Configuration in Dogs," CIRCULATION, 1988; vol. 78, No. 5, pp. 1288–1297.

James L. Cox, M.D., Ed., "Seminars in Thoracic and Cardiovascular Surgery: The Maze Procedure for Atrial Fibrillation," 2000, vol. 12, No. 1.

Lauran Neergaard, "Slicing a Heart to Make It Beat," Article from The Associated Press, Mar. 26, 1998 Website (www.nando.com/newsroom/ntn/health/032698/health24_22737_body.html).

Yoshito Inoue, et al., "Video Assisted Thoracoscopic and Cardioscopic Radiofrequency Maze Ablation," Asaio Journal, 1997, pp. 334–337.

Yoshito Inoue, et al., Abstract, "Video Assisted Thoracoscopic and Cardioscopic Radiofrequency Maze Ablation," Asaio Journal, 1997.

Mary O. Palazzo, RN, MS, CCRN, "What You Need To Know—a–fib 101," from the Atrial Fibrillation Page Website (www.members.aol.com/mazem/afib101.htm) Jun. 5, 2000.

Mary O. Palazzo, RN, MS, CCRN, "What You Need To Know—maze FAQ," from the Atrial Fibrillation Page Website (www.members.aol.com/mazem/mazefaq.htm) Nov. 25, 1999.

Mary O. Palazzo, RN, MS, CCRN, "What You Need To Know—maze FAQ," from the Atrial Fibrillation Page Website (www.members.aol.com/mazem/mazefaq.htm) Jun. 21, 2000.

Stuart P. Thomas, et al., "Mechanism, Localization and Cure of Atrial Arrhythmias Occurring After a New Intraoperative Endocardial Radiofrequency Ablation Procedure for Atrial Fibrillation," Journal of the American College of Cardiology, 2000, vol. 35, No. 2, pp. 442–450.

Ivan M. Robbins, M.D., et al., "Pulmonary Vein Stenosis After Catheter Ablation of Atrial Fibrillation," Circulation, 1998; 98:1769–1775.

Akira t. Kawaguchi, et al., "Factors Affecting Rhythm After the Maze Procedure for Atrial Fibrillation," CIRCULATION, 1998; vol. 78, No. 5, pp. 1288–1296.

Taijiro Sueda, et al., "Simple Left Atrial Procedure for Chronic Atrial Fibrillation Associated with Mitral Valve Disease," The Annals of Thoracic Surgery, 1996:62:1796–1800.

Berjano, Enrique J. et al. "Bipolar Electrosurgery With Long Electrodes for RF Coagulation of Atrial Tissue" Proceedings 19th International Conference—IEEE/EMBS Oct. 30–Nov. 2, 1997 Chicago, Il. USA. pp. 2528–2530.

* cited by examiner

METHOD FOR TRANSMURAL ABLATION

CROSS REFERENCE TO RELATED APPLICATION

This application is a continuation of application Ser. No. 09/747,609 filed on Dec. 22, 2000, now U.S. Pat. No. 6,546,935 which claims the benefit of provisional application Serial No. 60/200,072 filed on Apr. 27, 2000. The above applications are incorporated herein by reference.

BACKGROUND OF THE INVENTION

Atrial fibrillation is the most common heart arrhythmia in the world, affecting over 2.5 million people in the United States alone. Ablation of cardiac tissue, in order to create scar tissue that poses an interruption in the path of the errant electrical impulses in the heart tissue, is a commonly performed procedure to treat cardiac arrhythmias. Such ablation may range from the ablation of a small area of heart tissue to a series of ablations forming a strategic placement of incisions in both atria to stop the conduction and formation of errant impulses.

Ablation has been achieved or suggested using a variety of techniques, such as freezing via cryogenic probe, heating via RF energy, surgical cutting and other techniques. As used here, "ablation" means the removal or destruction of the function of a body part, such as cardiac tissue, regardless of the apparatus or process used to carry out the ablation. Also, as used herein, "transmural" means through the wall or thickness, such as through the wall or thickness of a hollow organ or vessel.

Ablation of cardiac tissue may be carried out in an open surgical procedure, where the breastbone is divided and the surgeon has direct access to the heart, or through a minimally invasive route, such as between the ribs or via catheter that is introduced through a vein, and into the heart.

Prior to any ablation, the heart typically is electronically mapped to locate the point or points of tissue which are causing the arrhythmia. With minimally invasive procedures such as via a catheter, the catheter is directed to the aberrant tissue, and an electrode or cryogenic probe is placed in contact with the endocardial tissue. RF energy is delivered from the electrode to the tissue to heat and ablate the tissue (or the tissue may be frozen by the cryogenic probe), thus eliminating the source of the arrhythmia.

Common problems encountered in this procedure are difficulty in precisely locating the aberrant tissue, and complications related to the ablation of the tissue. Locating the area of tissue causing the arrhythmia often involves several hours of electrically "mapping" the inner surface of the heart using a variety of mapping catheters, and once the aberrant tissue is located, it is often difficult to position the catheter and the associated electrode or probe so that it is in contact with the desired tissue.

The application to the inside of the heart chamber of either RF energy or ultra-low temperature freezing also carries several risks and difficulties. It is very difficult to determine how much of the catheter electrode or cryogenic probe surface is in contact with the tissue since catheter electrodes and probes are cylindrical and the heart tissue cannot be visualized clearly with existing fluoroscopic technology. Further, because of the cylindrical shape, some of the exposed electrode or probe area will almost always be in contact with blood circulating in the heart, giving rise to a risk of clot formation.

Clot formation is almost always associated with RF energy or cryogenic delivery inside the heart because it is difficult to prevent the blood from being exposed to the electrode or probe surface. Some of the RF current flows through the blood between the electrode and the heart tissue and this blood is coagulated, or frozen when a cryogenic probe is used, possibly resulting in clot formation. When RF energy is applied, the temperature of the electrode is typically monitored so as to not exceed a preset level, but temperatures necessary to achieve tissue ablation almost always result in blood coagulum forming on the electrode.

Overheating or overcooling of tissue is also a major complication, because the temperature monitoring only gives the temperature of the electrode or probe, which is, respectively, being cooled or warmed on the outside by blood flow. The actual temperature of the tissue being ablated by the electrode or probe is usually considerably higher or lower than the electrode or probe temperature, and this can result in overheating, or even charring, of the tissue in the case of an RF electrode, or freezing of too much tissue by a cryogenic probe. Overheated or charred tissue can act as a locus for thrombus and clot formation, and over freezing can destroy more tissue than necessary.

It is also very difficult to achieve ablation of tissue deep within the heart wall. A recent study reported that to achieve a depth of ablation of 5 mm, it was necessary to ablate an area almost 8 mm wide in the endocardium. See, "Mechanism, Localization, and Cure of Atrial Arrhythmias Occurring After a New Intraoperative Endocardial Radiofrequency Ablation Procedure for Atrial Fibrillation," Thomas, et al., *J. Am. Coll. Cardiology*, Vol. 35, No. 2, 2000. As the depth of penetration increases, the time, power, and temperature requirements increase, thus increasing the risk of thrombus formation.

In certain applications, it is desired to obtain a continuous line of ablated tissue in the endocardium. Using a discrete or point electrode or probe, the catheter must be "dragged" from point to-point to create a line, and frequently the line is not continuous. Multielectrode catheters have been developed which can be left in place, but continuity can still be difficult to achieve, and the lesions created can be quite wide.

Because of the risks of char and thrombus formation, RF energy, or any form of endocardial ablation, is rarely used on the left side of the heart, where a clot could cause a serious problem (e.g., stroke). Because of the physiology of the heart, it is also difficult to access certain areas of the left atrium via an endocardial, catheter-based approach.

Recently, epicardial ablation devices have been developed which apply RF or microwave energy to the outer wall of the heart to ablate tissue. These devices do not have the same risks concerning thrombus formation. However, it is still difficult to create long, continuous lesions, and it is difficult to achieve good depth of penetration without creating a large area of ablated tissue.

As noted above, other forms of energy have been used in ablation procedures, including ultrasound, cryogenic ablation, and microwave technology. When used from an endocardial approach, the limitations of all energy-based ablation technologies to date are the difficulty in achieving continuous transmural lesions, and minimizing unnecessary damage to endocardial tissue. Ultrasonic and RF energy endocardial balloon technology has been developed to create circumferential lesions around the individual pulmonary veins. See e.g., U.S. Pat. No. 6,024,740 to Lesh et al. and U.S. Pat. Nos. 5,938,660 and 5,814,028 to Swartz et al. However, this technology creates rather wide (greater than 5 mm) lesions which could lead to stenosis (narrowing) of the pulmonary veins. See, "Pulmonary Vein Stenosis after Catheter Ablation of Atrial Fibrillation," Robbins, et al., *Circulation*, Vol. 98, pages 1769–1775, 1998. The large lesion area can also act as a locus point for thrombus formation. Additionally, there is no feedback to determine when full transmural ablation has been achieved. Cryogenic ablation has been attempted both endocardially and epicardially (see e.g., U.S. Pat. Nos. 5,733,280 to Avitall, 5,147,355 to Friedman et al., and 5,423,807 to Milder, and WO 98/17187, the latter disclosing an angled cryogenic probe, one arm of which is inserted into the interior of the heart through an opening in the heart wall that is hemostatically sealed around the arm by means of a suture or staples), but because of the time required to freeze tissue, and the delivery systems used, it is difficult to create a continuous line, and uniform transmurality is difficult to verify.

Published PCT applications WO 99/56644 and WO 99/56648 disclose an endocardial ablation catheter with a reference plate located on the epicardium to act as an indifferent electrode or backplate that is maintained at the reference level of the generator. Current flows either between the electrodes located on the catheter, or between the electrodes and the reference plate. It is important to note that this reference plate is essentially a monopolar reference pad. Consequently, this backplate is not intended to ablate tissue. Instead, the ablation begins at the electrodes within the endocardium, and travels through the heart tissue either to another endocardial electrode, or to the backplate. Tissue ablation proceeds from the endocardium outward to the epicardium. Other references disclose epicardial multielectrode devices that deliver either monopolar or bipolar energy to the outside surface of the heart.

It is important to note that all endocardial ablation devices that attempt to ablate tissue through the full thickness of the cardiac wall have a risk associated with damaging structures within or on the outer surface of the cardiac wall. As an example, if a catheter is delivering energy from the inside of the atrium to the outside, and a coronary artery, the esophagus, or other critical structure is in contact with the atrial wall, the structure can be damaged by the transfer of energy from within the heart to the structure. The coronary arteries, esophagus, aorta, pulmonary veins, and pulmonary artery are all structures that are in contact with the outer wall of the atrium, and could be damaged by energy transmitted through the atrial wall. Furthermore, when performing ablation on a beating heart, either endocardially, or epicardially, it is very difficult to stabilize the ablation element in one position relative to the moving heart tissue.

Accordingly, it is the object of the present invention to provide an improved method for making transmural ablations to heart tissue.

It is a related object to provide a method for making transmural ablation in heart tissue that minimizes unnecessary damage to the heart tissue.

It is a further object to provide a method for making transmural ablation in heart tissue that creates continuous lesions in a single step.

It is a further object of this invention to provide a method to stabilize the ablation element relative to the tissue being ablated during a beating heart procedure.

It is a further object of this invention to provide an improved method for minimizing the amount of ablated tissue and maximizing current density.

It is a further object of this invention to provide a method for rapidly creating a lesion around the pulmonary veins without excessive clamp time.

It is a further object of this invention to provide a method for creating a series of lesions to isolate one or both pulmonary veins without stopping blood flow through the veins.

SUMMARY OF THE INVENTION

These objects, and others which will become apparent upon reference to the following detailed description and attached drawings, are achieved by a method that creates an electrically isolating line of ablated tissue on a hollow organ or vessel that includes the steps of bringing the opposing walls of the organ into contact with each other along a line and passing sufficient electrical current through both walls along the line of contact to form a continuous line of ablated tissue through both walls of the tissue in a single step without bonding the walls together.

More specifically, the invention comprises a method for at least partially electrically isolating a pulmonary vein from a heart atrium comprising the steps of clamping together the opposed walls of the atrium proximal to the pulmonary vein so that the opposed walls are in contact with each other along a line. The tissue in both walls along the line of contact is then ablated to form a corresponding line of ablated tissue without bonding the walls together. Clamping of the tissue insures that the ablation element is fixed with respect to the tissue intended for ablation. Clamping of the tissue between the RF electrodes minimizes the tissue being ablated because the volume of the tissue in a direct path between the electrode is minimized. The energy is more concentrated because the two poles are close together. These steps are performed a plurality of times, each time partially circumscribing the pulmonary vein, with the steps being performed a sufficient number of times to form a series of lines that substantially fully circumscribe the pulmonary vein. Preferably, the method is performed in a single step, with a continuous lesion being formed that circumscribes one or both of the pulmonary veins. If one or both pulmonary veins are isolated in a single step, the blood flow through the veins is cut off. If the blood flow through the pulmonary veins is cut off for several minutes, severe complications can result as a result of the blood stasis, including clotting within the veins. The delivery of RF energy through the clamped tissue is extremely rapid, typically less than 30 seconds, because the volume of ablated tissue is minimized, and the energy concentration is maximized. If a sequence of overlapping lesions is created to isolate the pulmonary veins, then the blood flow is not cut off, and the problems associated with the blood stasis are avoided.

In a still further method of the invention, a clamping device with opposing jaws moveable between open and closed positions is provided, and either the atrium or pulmonary vein is positioned between the opposing jaws of the clamping device. The jaws are then closed to form a clamping area that has a width so that the opposed walls of the atrium or pulmonary vein come into contact along the clamping area, with the clamping area being expressed of blood. The tissue clamped between the jaws is then ablated along a line that is substantially narrower than the clamping area to create a line of ablated tissue through both of the walls of the atrium or pulmonary vein without bonding them together.

DETAILED DESCRIPTION OF THE PREFERRED EMBODIMENTS

With reference to the present invention, the compression of the atrial tissue is important because it insures that the exposed electrode surface or cryogenic probe is not in contact with any tissue or blood except the clamped tissue to be ablated. Specifically, the clamping of the tissue between the electrodes or cryogenic probes insures that the conductive or cooled area is only in contact with the clamped tissue. The compressed tissue acts to isolate the electrically active or cryogenically cooled surface, and prevents inadvertent energy delivery to other parts of the heart or blood. The outside temperature of the jaws can easily be monitored to insure that the temperature of the insulation in contact with blood remains below a critical temperature (40° C., for example).

In one form of the invention, transmural ablation using RF energy is accomplished by providing an atrial ablation device having a lower "j" clamp/electrode element and placing it on the atrial tissue below the pulmonary veins.

Once the lower jaw is positioned to span across both pulmonary veins, an upper clamp/electrode element is introduced, and the clamp assembly "J" is worked back onto the atrial tissue. Once the jaws are positioned below the ostia of the pulmonary veins, the tissue is partially clamped, allowing continued flow from the pulmonary veins to the left atrium. Once the clamps are safely away from the pulmonary vein tissue, and onto atrial tissue, the clamps are closed together to compress the tissue. Once the tissue is compressed, bipolar RF energy is used to ablate the clamped atrial tissue. The clamps are then removed, the lesion having been created.

Figure 1:
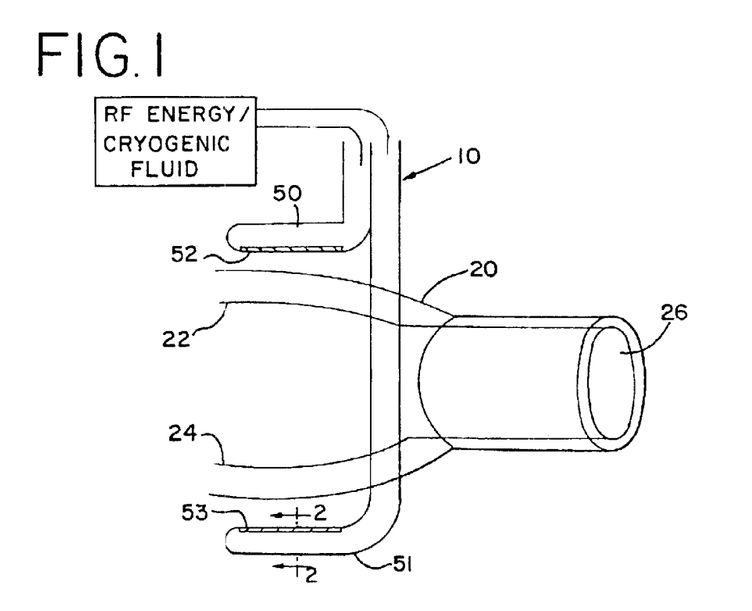
FIG. 1 is a schematic view showing a procedure in accordance with the present invention utilizing ablation elements operatively connected to either a source of RF energy or cryogenic fluid.
Figure 2:
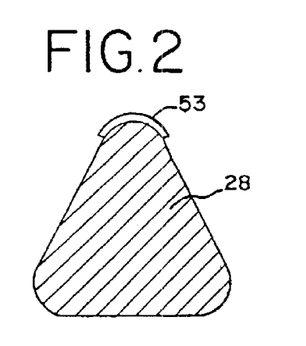
FIG. 2 is a cross-section of an ablation element for use in the present invention taken along lines 2—2 of FIG. 1.
Figure 3:
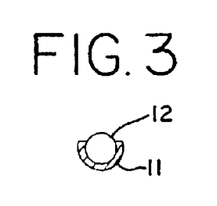
FIGS. 3–6 show alternate configurations for the ablation elements of FIG. 2.
Figure 4:
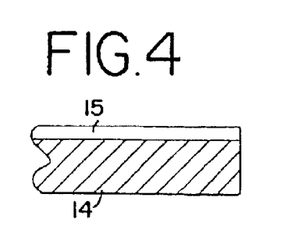
Figure 5:
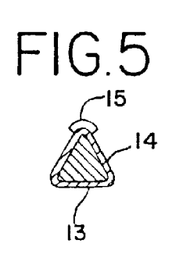
Figure 6:
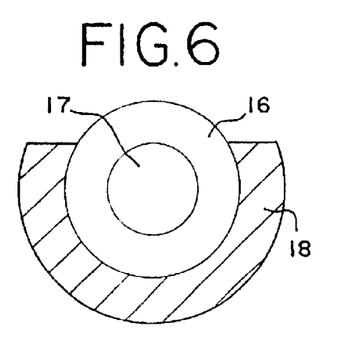
Figure 7:
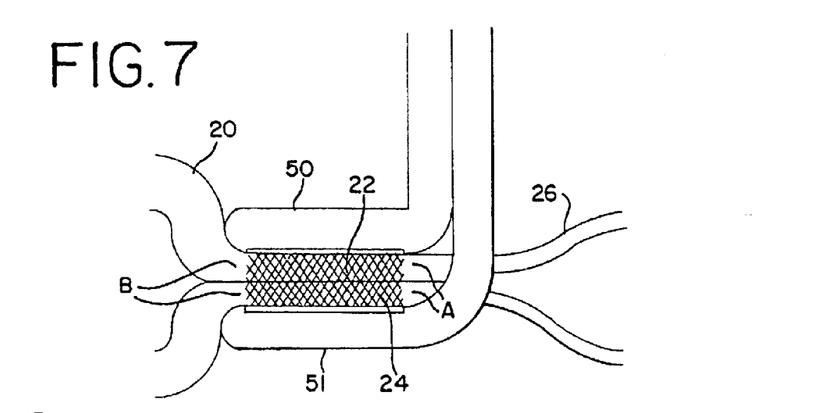
FIG. 7 shows a further step in the inventive procedure in which tissue is clamped between the ablation elements.

Turning now to the figures of the drawings, a method embodying the present invention is shown schematically in FIG. 1. A clamping type device 10 is provided to group the two walls 22, 24 of the atrium 20, and delivers bipolar RF energy through both walls held between the two upper and lower clamp jaws 50, 51. FIG. 1 shows the upper and lower clamp jaws 50, 51 and electrodes 52, 53 positioned above and below atrial tissue 22, 24, distal to the pulmonary veins. FIG. 2, Section 2—2 of FIG. 1, shows a cross-section of the clamping member including the insulator 28 and electrode 53. Alternate configurations of the clamping members are shown in FIGS. 3–6 and 32. FIG. 3 shows a cross section of the electrode consisting of an insulating layer 11, and a conductive strip 12. The electrode of FIG. 3 may be constructed of a tungsten wire as the conductive material 12, with polyamide as the insulating material 11. The conductive strip is created by exposing a part of the tungsten wire through the polyamide. FIGS. 4 and 5 show an alternate electrode construction consisting of a carbon fiber element 13, and an insulating material 14, such as ABS. The conductive strip 15 may be comprised of a copper/gold electrode plated onto the ABS. FIG. 6 shows a cross section of yet another possible electrode design where the conductive material 16 consists of a stainless steel needle with lumen 17 and insulating material 18. FIG. 7 shows the jaws 50, 51 clamping and ablating the atrial tissue 20 distal to the pulmonary veins 26. Proximal point A is clamping and ablating the atrial tissue distal to the pulmonary veins. Proximal point A is the most proximal point of ablated tissue on both the upper and lower atrial wall. Distal point B is the most distal point of ablated tissue on both the upper and lower atrial wall.

Figures 8, 9:
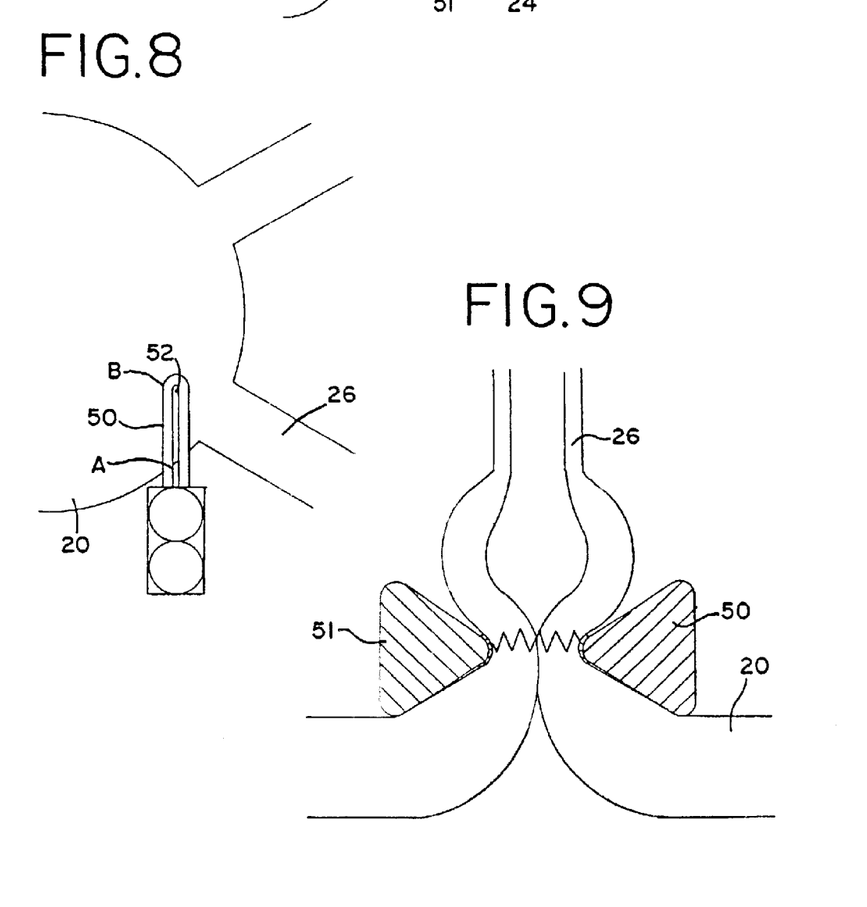
FIGS. 8–12 schematically illustrate the inventive procedure so as to make a transmural lesion that fully circumscribes a pulmonary vein, with FIG. 9 showing a cross-sectional view of the clamp/ablation element in contact with the atrial tissue to express blood from the clamped area.
Figure 10:
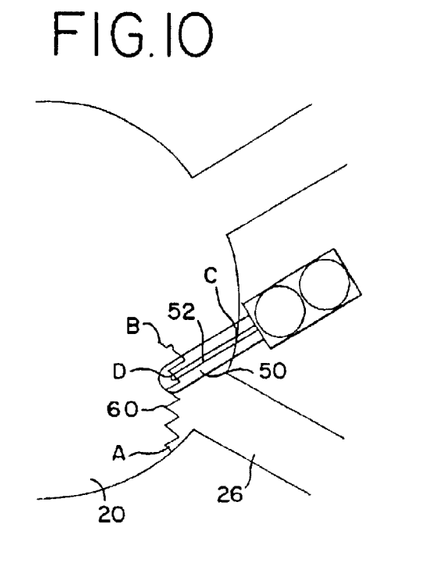

FIGS. 8–12 show the inventive procedure that fully circumscribes a pulmonary vein with transmural lesions. FIG. 8 shows a top view of the instrument jaws positioned for a 2-step isolation of a single pulmonary vein. The lower jaw is directly beneath the upper jaw, and is not shown. Proximal point A and distal point B correspond to FIG. 7.

Figures 23, 24, 26:
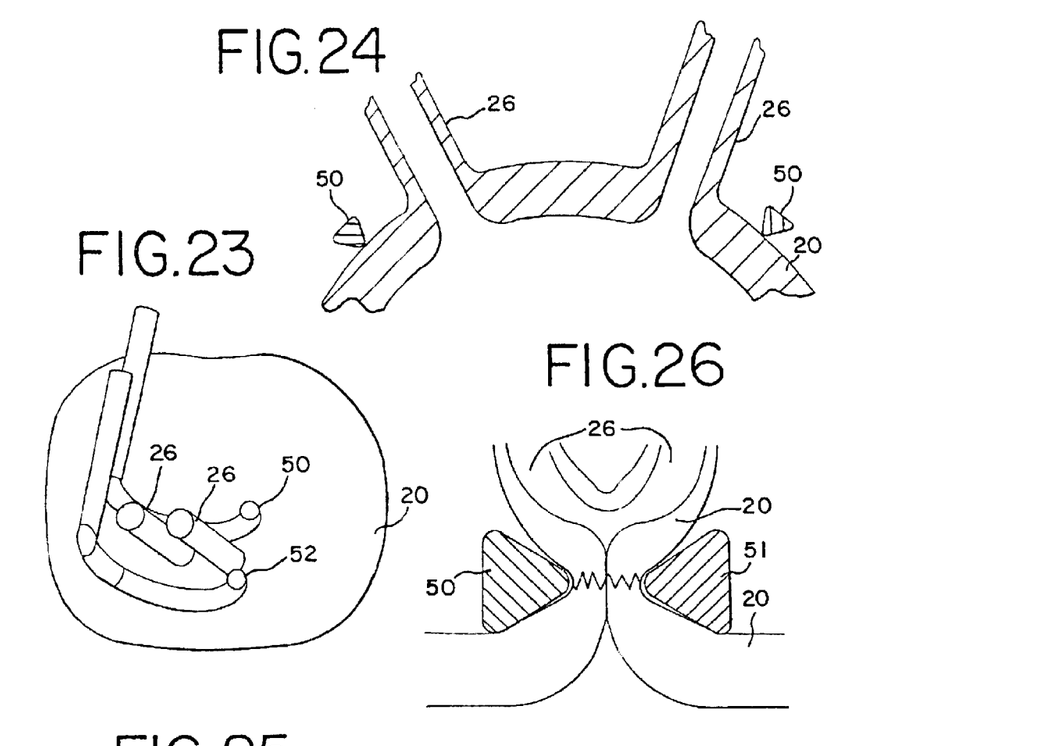
FIGS. 23–27 illustrate a further procedure in which a transmural lesion is made so as to circumscribe both pulmonary veins.
Figures 25, 27:
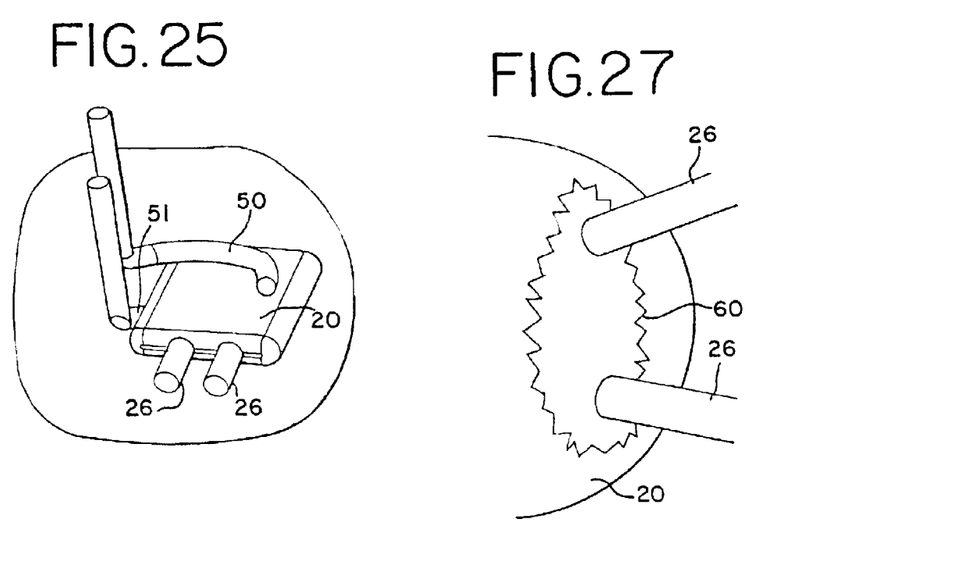
Figures 28, 29:
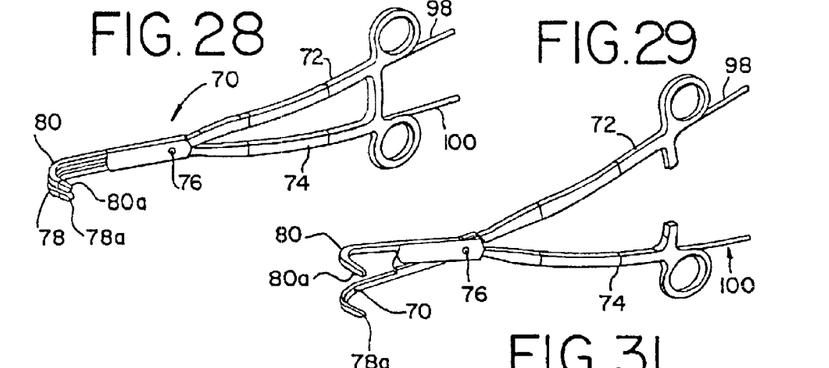
FIG. 28 is a perspective view of a further embodiment of a grasper in accordance with the present invention showing the grasper in its "closed" position.
FIG. 29 is a perspective view of the grasper of FIG. 28 with the grasper in its "open" position.
Figure 30:
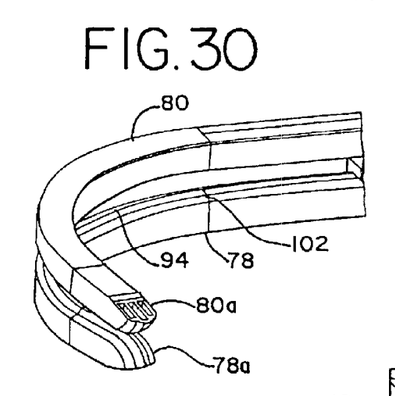
FIG. 30 is an enlarged perspective view of the working position of the grasper of FIG. 28 with the grasper jaws in the "closed" position.
Figure 31:
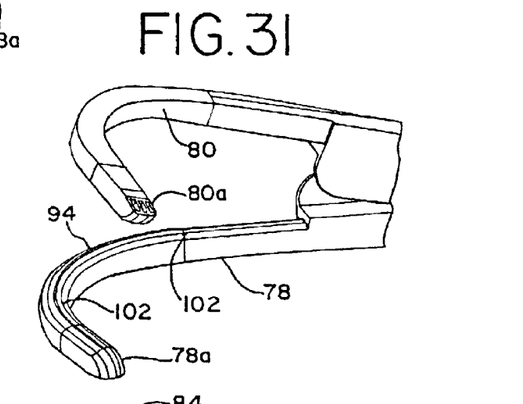
FIG. 31 is an enlarged perspective view of the working portion of the grasper of FIG. 28 with the grasper jaws in the "open" position.

FIG. 9 shows a cross-sectional view of the jaws clamping and ablating atrial tissue. Importantly, FIG. 9 shows that the electrode/clamp configuration provides a clamped zone of tissue that is wider than the zone of ablated tissue. This is achieved by using an electrode width that is narrower than the clamped tissue width. As shown in FIG. 9 (and better illustrated in FIG. 26), the electrode forms the apex of the triangular clamping member. Other convex shapes are also contemplated.

The wider zone of clamped tissue serves several purposes. When the clamping members are closed onto tissue, any blood in the clamped zone is squeezed or expressed out. Further, the distance between the electrodes is minimized, so that the ablation zone remains narrow. It is important to isolate the blood from the ablation zone to avoid creating thrombus. Accordingly, a clamped zone that isolates the ablation zone from the blood minimizes the temperature at the periphery of the ablation zone and will reduce the likelihood of the formation of thrombus by the blood in contact with the clamped zone.

Figure 11:
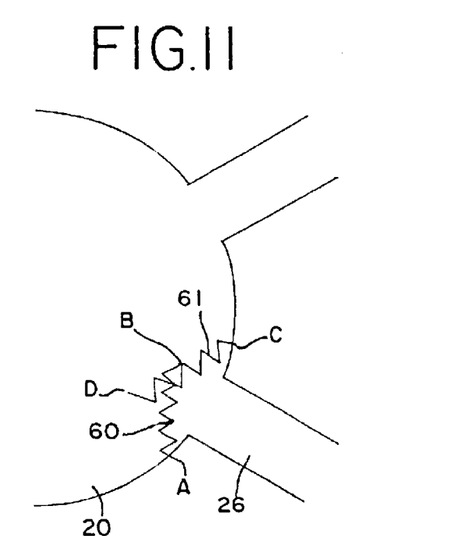
Figure 12:
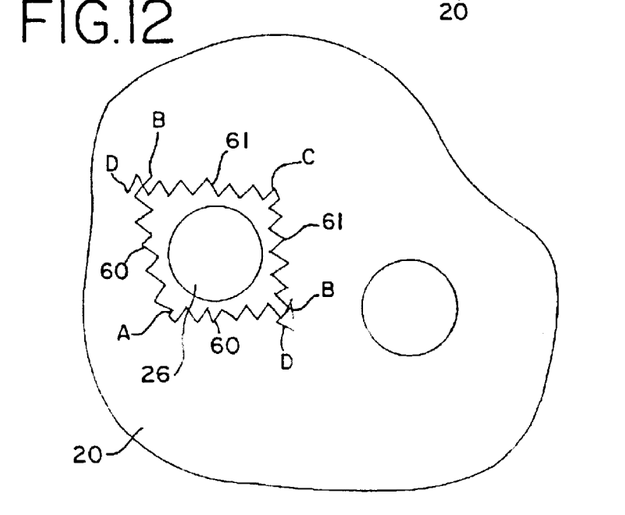
Figure 13:
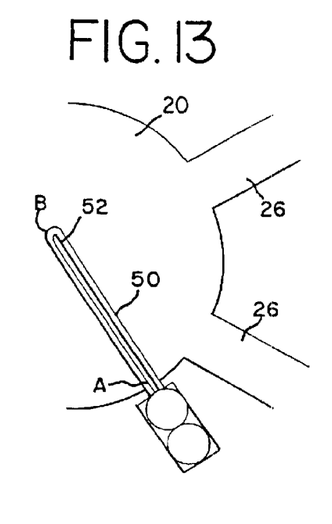
FIGS. 13–17 show a further method according to the present invention in which transmural lesions are made so as to circumscribe both pulmonary veins.
Figure 14:
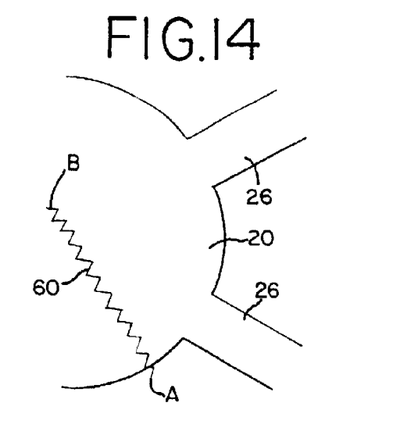
Figure 15:
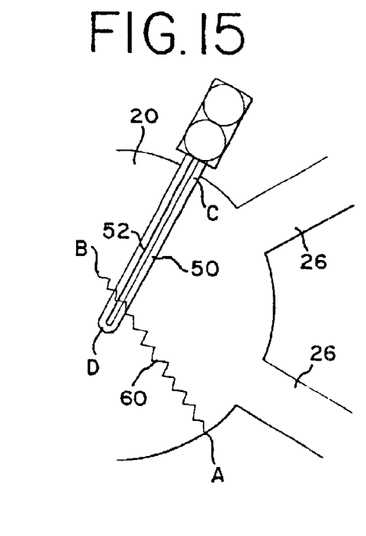
Figure 16:
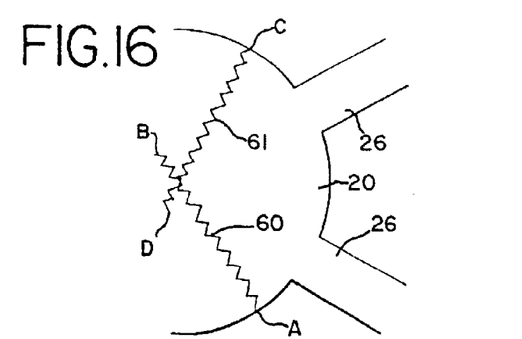
Figure 17:
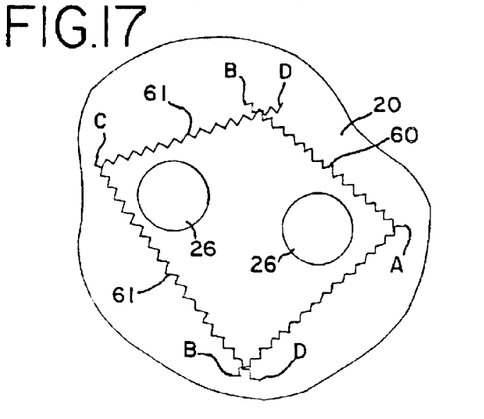

Once tissue has been fully ablated with the clamp in the position shown in FIG. 8, an ablation line of tissue on both upper and lower atrial walls is created. This is shown as ablation line 60 in FIG. 10. The clamp is then repositioned to the position shown in FIG. 10, so that the distal point D overlaps the ablation line 60. The tissue is clamped and ablated as shown in FIGS. 7 and 9, and a second ablation line 61 (FIG. 11) is formed on both the upper and lower atrial walls. Proximal point C and distal point D correspond to points A and B respectively. The full ablation line is shown in FIGS. 11 and 12 with points A–D as shown.

This "clamping" method and device for creating transmural lesions has a number of advantages. First, using a two step method as shown allows for clamping and ablation of atrial tissue without stopping the blood flow from the pulmonary vein. Secondly, by clamping both walls together, and delivering energy through the clamped tissue, the atrial tissue is not penetrated. Because the atrial tissue is not penetrated, a larger jaw can be used, and the clamping force can be much higher because of the increased stiffness of the jaw. Also, there is no concern of bleeding from an atrial puncture.

Another advantage of this method and device is that ablation of tissue within the pulmonary veins is avoided, as recent articles have shown that ablation of tissue within the pulmonary veins can cause pulmonary hypertension and stenosis. Specifically referring to FIGS. 13–17, a longer jaw could be used to create an ablation line through atrial tissue which electrically isolates both pulmonary veins using the same method.

Figures 18, 19, 21:
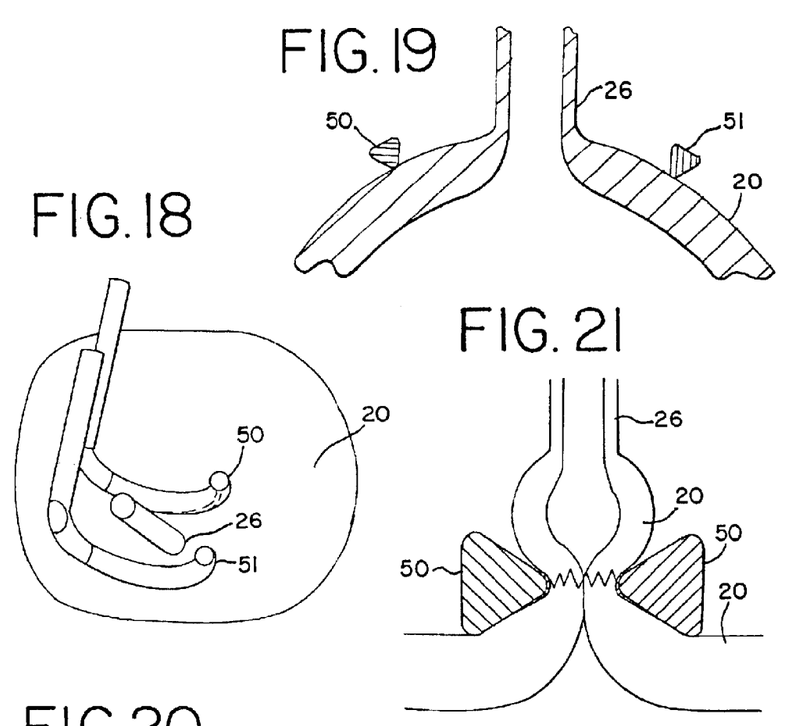
FIGS. 18–22 show a further procedure in which a transmural lesion is made so as to circumscribe a single pulmonary vein.
Figures 20, 22:
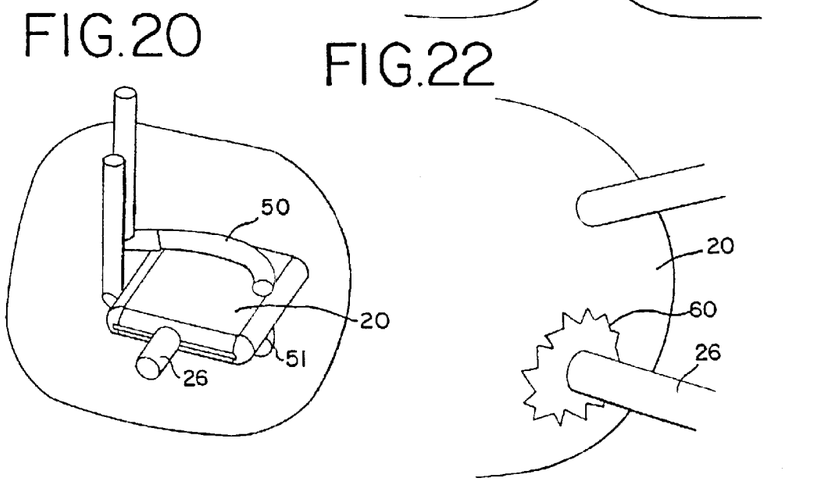

FIGS. 18–22 show the clamping device in a curved embodiment that creates a circumferential lesion around the pulmonary vein in one step. FIGS. 18 and 19 show the clamp jaws positioned around the pulmonary vein. FIGS. 20 and 21 show the device clamping and ablating atrial tissue proximal to the pulmonary vein. FIG. 22 shows the resulting ablation line 60.

FIGS. 23–27 show the same concept applied to a device and method for creating a lesion around both pulmonary veins. The advantage of this concept is that the entire lesion is created in one step. The disadvantage is that blood flow from the pulmonary vein(s) is cut off during ablation. Using a curved electrode also allows the user to ablate tissue more proximal to the pulmonary veins than would be possible with a straight electrode. Note that this curved type electrode could be used with a two step procedure as described above, using "left" and "right" curved devices to create a lesion which was more distal to the pulmonary veins. Note also that this method and device are not limited to use around the pulmonary veins, but could be used anywhere in the atrium that the clamp could be applied.

Turning to FIGS. 28–32, there is seen a further version of a cardiac grasper 70 in accordance with the present invention. The grasper 70 includes two ring handles 72, 74 joined together for relative movement by a pivot screw or pin 76. Each handle 72, 74 has a jaw member 78, 80 respectively associated therewith, each jaw being curved so that it has a major portion that is substantially perpendicular to the handles. This gives the grasper 70 an L-shaped appearance, with a working portion of the jaws being between approximately 3–8 cm in length.

Figure 32:
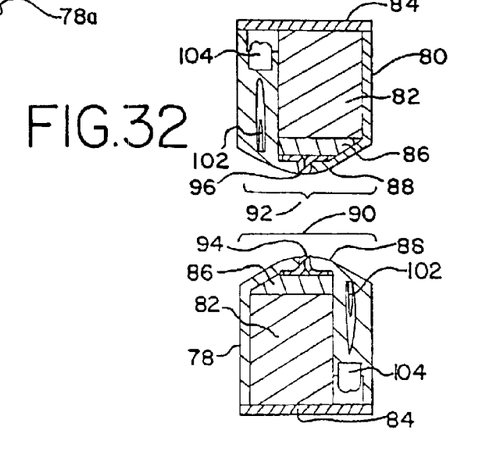
FIG. 32 is an enlarged cross-sectional view of the grasper jaws for the grasper of FIG. 28.

The grasper is made of a rigid material, such as stainless steel, and is substantially encased in a durable insulating material, such as ABS plastic. With reference to FIG. 32, which shows the opposed jaw members in cross section, the stainless steel structural support is designated 82. The structural support 82 is completely encased by insulating members 84, 86 and 88. The tips 78a, 80a of the jaws may be made of a soft, atraumatic material in order to reduce the likelihood of unintentional injury of tissue by the jaws.

In keeping with the invention, the grasper jaws have raised or convex, opposed tissue clamping surfaces, 90, 92, respectively, with each clamping surface, 90, 92 centrally supporting an electrode 94, 96, respectively, of opposite polarity. RF energy of opposite polarity is supplied to the electrodes 94, 96 through conductors 98, 100, which are connected to an RF generator. As with the previously-described jaw members, this electrode/clamp configuration provides a clamped zone of tissue that is significantly wider than the zone of ablated tissue created by the opposed electrodes. This causes for any blood in the clamp zone to be squeezed or expressed out of the ablation zone, thus reducing the likelihood of thrombus formation, as well as minimizing the distance between the electrodes, so that the ablation zone remains narrow. The clamping also eliminates the cooling effect of circulating blood.

With reference to FIG. 32, the electrodes 94, 96 have a T-shaped cross section, with the cross portion of the T resting on the insulating member 88 and the upright portion of the T protruding through a narrow opening in the insulating member 84, thus creating an exposed electrode surface that contacts the tissue grasped between the jaws. In practice, the electrodes are preferably made of gold-plated copper and extend along substantially the entire working surface of the jaw members. The exposed portions of the electrode are generally between approximately 0.12–0.6 mm in width. In keeping with a further aspect of the invention, the graspers may provide feedback that permits the user to gauge the completeness (i.e., degree of transmurality) of the ablation. During RF energy application to the tissue to be ablated, the current and voltage applied to the tissue are measured, and the impedance calculated and stored. Based upon a function of the impedance (e.g., its value, the change in value, or the rate of change in value) it is determined whether ablation is complete and transmural. See e.g., U.S. Pat. No. 5,403,312, which is incorporated by reference herein. Indicator lights or other types of signals (e.g., audible) may be associated with the grasper to correspond to the degree of ablation determined by the impedance feedback system. For example, once the impedance reaches a certain level for a certain period of time, a red light may be activated to signal that ablation is complete.

In keeping with another aspect of the invention, a feedback system for determining the temperature of the ablated tissue is also provided. To this end, the jaws include a series of thermocouples 102 that are supported in the insulating member 84 and protrude slightly therethrough so as to engage any tissue clamped between the jaws 72, 74. Wires 104 are attached to the thermocouples 102 to transmit the information received to a remote location. Again, a visual or other indicator may be provided to alert the user that a certain predetermined critical temperature (e.g., 40° C.) has been reached.)

Thus, it can be seen that a transmural ablation device and method have been provided that overcome the limitations of the prior art. First, current technology involves ablation devices deliver ablation energy to either the inside (endocardium) or outside (epicardium) of the heart. Using these techniques, the tissue ablation proceeds from one wall of the heart through the tissue to the opposite wall. To date, there has been no reliable way to consistently achieve lesions that penetrate the full thickness of the atrial wall (transmural lesions), and there has been no way to determine either continuity or transmurality of these lesions. If the lesion does not penetrate through enough of the atrial wall, conduction can still occur, and the lesion does not fully block the electrical signals that are causing the arrhythmia. Using an endocardial approach, if the lesion penetrates too far through the wall, critical structures such as coronary arteries, veins, or the esophagus can be damaged on the outside of the heart. Using an epicardial approach, if the lesion penetrates too far, blood can be coagulated, or critical structures such as valves, nodes, or connective tissue can be damaged on the inside of the heart.

There has also been no reliable and consistent way to safely achieve fully continuous, long (greater than 1 cm) lesions in the atrial wall without a high risk of thrombus, damage to critical structures, or extensive damage to the atrial tissue.

The present invention overcomes these shortcomings because the conductive area of each electrode is very narrow compared to the width of the clamped area. As a result, the thermal damage to the tissue is minimal. In contrast, current technology uses catheter electrodes which are typically 1 or 2 mm diameter requiring a lesion width of almost 8 mm to achieve a depth of 5 mm. Using the present invention, a lesion depth of 5 mm with a width of less than 2 mm can be achieved. This aspect of the invention allows for longer linear lesions with less power delivery because less tissue is being heated. There is, therefore, considerably less damage to healthy atrial tissue for a lesion of a given depth and length. Recent efforts in creating linear lesions using endocardial electrodes resulted in ablation of over 20% of the atrial endocardium, and a commensurate decrease in atrial contractility.

Another advantage of this device is that ablation can be done on a beating heart. Once the device is clamped onto the atrial wall, the position of the electrodes can be verified by visually inspecting the position of the outer electrode before delivery of RF energy. The clamping insures the electrodes will not move relative to the atrial tissue as the ablation proceeds. If the clamping pressure is higher than the atrial pressure, then clamping over a coronary artery would cut off blood flow, and the resulting change in the EKG would act as a warning to the user prior to applying RF energy. The clamping will prevent any movement of the electrodes relative to the heart wall, and RF energy can be applied with confidence that the ablated tissue will be contained completely between the two electrodes.

Another important feature of this device is that the energy transfer is limited to the tissue clamped between the two electrodes. The insulated electrodes protect structures on the outside of the heart from being exposed to RF energy. Because of this limitation of current flow, damage to critical structures can be avoided.

Another advantage of this device is that it can easily be adapted to a minimally invasive thoracoscopic approach. The device shown has been reduced to a 10 mm diameter device. Using video thoracoscopy, the device could be introduced through a small intracostal incision, and used to create fully transmural linear lesions on a beating heart, possibly under local anesthesia on an anesthetized patient.

Accordingly, a method for performing transmural ablation has been provided that meets all the objects of the present invention. While the invention has been described in terms of certain preferred methods, there is no intent to limit the invention to the same. Instead it is to be defined by the scope of the appended claims.

What is claimed is:

1. A method for at least partially electrically isolating a pulmonary vein from a heart atrium, the atrium having opposed walls, comprising:

bringing together opposed walls of the atrium proximal to a pulmonary vein into contact with each other along a line;

ablating the tissue in both walls along the line of contact sufficient to form a corresponding line of ablated tissue across both walls of the tissue without bonding the walls together;

performing the foregoing steps a plurality of times, each time partially circumscribing the pulmonary vein and performing the steps a sufficient number of times to form a series of lines of ablated tissue that together substantially fully circumscribes a pulmonary vein.

2. The method of claim 1 which comprises performing the steps a plurality of times to form a series of lines of ablated tissue that together substantially fully circumscribe two pulmonary veins.

3. A method for creating a lesion to electrically isolate the pulmonary veins from the atrium, said pulmonary veins and atrium each being hollow and having opposed walls, the method comprising:

a) providing a clamping device with opposing jaws capable of grasping tissue;

b) positioning one of either said atrium or pulmonary vein between the opposing jaws of the clamping device;

c) closing the jaws on the one of either said atrium or pulmonary vein to form a clamping area having a width so that the opposed walls come into contact along the clamping area and said clamping area width is expressed of blood between the opposed walls; and d) ablating the tissue clamped between the jaws to create a line of ablated tissue through both of the walls without bonding them together.

4. The method of claim 3 in which the jaws of the clamping device include a tissue engaging surface shaped to clamp the opposed walls most tightly along the line of ablated tissue.

5. The method of claim 3 in which the tissue engaging surface of each jaw is convex in cross-sectional shape.

6. The method of claim 3 in which the jaws of the clamping device include a generally flat tissue engaging surface.

7. The method of claim 3 further comprising the step of determining the degree of tissue ablation.

8. The method of claim 7 wherein the degree of tissue ablation is determined by measuring the temperature of the ablated tissue.

9. The method of claim 7 wherein the degree of tissue ablation is determined by measuring the electrical resistance of the ablated tissue.

10. A method of creating a transmural ablation line in atrial tissue comprising:

providing a tissue grasping apparatus comprising first and second grasping jaws, each jaw including a raised electrode and a clamping surface receding from the electrode in face-to-face relation with the electrode and clamping surface of the other jaw, said grasping jaws being relatively moveable, with the clamping surfaces of said jaws comprising an insulating material, the raised face-to-face electrodes being of opposite polarity and connected to a power source for providing an electrical current between said electrodes;

closing the jaws of the tissue grasping apparatus on the atrial tissue proximal to the pulmonary veins so that portions of the atrium wall are brought together and the electrodes are entirely in contact with the atrial tissue to be ablated;

creating a current flow between said electrodes and through the atrial tissue located between the closed jaws to create a transmural ablation through said atrial tissue.

11. A method for creating a lesion to isolate a pair of pulmonary veins from the body of the atrium, comprising:

a) providing a clamping device with opposing jaws capable of grasping tissue;

b) positioning the atrial tissue proximal to the pulmonary veins between the jaws;

c) closing the jaws to compress the atrial tissue so the opposed walls come into contact along a clamping area; and d) ablating the tissue clamped between the jaws to create a line of ablated tissue through both of the walls without bonding the walls together.

12. A method for creating a lesion to electrically isolate the pulmonary veins from the atrium, said pulmonary veins and atrium each being hollow and having opposed walls, the method comprising:

a) providing a clamping device with opposing jaws capable of grasping tissue;

b) positioning the atrium proximal to a pulmonary vein between the opposing jaws of the clamping device;

c) closing the jaws on the atrium to form a clamping area having a width so that the opposed walls come into contact along the clamping area and said clamping area width is substantially expressed of blood between the opposed walls; and d) ablating the tissue clamped between the jaws to create a line of ablated tissue through both of the walls without bonding them together.

13. The method of claim 12 in which the jaws of the clamping device include a tissue engaging surface shaped to clamp the opposed walls most tightly along the line of ablated tissue.

14. The method of claim 12 in which the tissue engaging surface of each jaw is convex in cross-sectional shape.

15. The method of claim 12 in which the jaws of the clamping device include a generally flat tissue engaging surface.

16. The method of claim 12 further comprising the step of determining the degree of tissue ablation.

17. The method of claim 16 wherein the degree of tissue ablation is determined by measuring the temperature of the ablated tissue.

18. The method of claim 16 wherein the degree of tissue ablation is determined by measuring the electrical resistance of the ablated tissue.

19. A method of creating a transmural ablation line in atrial tissue comprising:

providing a tissue grasping apparatus comprising first and second grasping jaws, each jaw including a raised electrode and a clamping surface receding from the electrode in face-to-face relation with the electrode and clamping surface of the other jaw, said grasping jaws being relatively moveable, with the clamping surfaces of said jaws comprising an insulating material, the raised face-to-face electrodes being of opposite polarity and connected to a power source for providing an electrical current between said electrodes;

closing the jaws of the tissue grasping apparatus on the atrial tissue proximal to the pulmonary veins so that the jaws are closed on the wall of the atrium to compress the wall together in opposition along a line and the electrodes are in contact with the atrial tissue to be ablated;

creating a current flow between said electrodes and through the atrial tissue located between the closed jaws to create a transmural ablation through said atrial tissue.

20. The method of claim 19 wherein current flow is created between the electrodes and simultaneously through the opposed portions of the wall of the atrium along the line.

21. A method for creating a lesion with RF energy to isolate a pair of pulmonary veins from the body of the atrium, comprising:

a) providing a clamping device with opposing jaws capable of grasping tissue;

b) positioning the atrial tissue proximal to the pulmonary veins between the jaws;

c) closing the jaws to compress the atrial tissue so the opposed walls come into contact along a clamping area; and d) ablating the tissue clamped between the jaws with RF energy by passing electrical current between the jaws to create a line of ablated tissue through both of the walls without bonding the walls together.

* * * * *